(12) United States Patent
Tyvoll et al.

(10) Patent No.: US 7,389,879 B2
(45) Date of Patent: Jun. 24, 2008

(54) SORTING PARTICLES

(75) Inventors: David Tyvoll, La Jolla, CA (US); Winthrop D. Childers, San Diego, CA (US); Paul Crivelli, San Diego, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 467 days.

(21) Appl. No.: 10/763,112

(22) Filed: Jan. 21, 2004

(65) Prior Publication Data

US 2005/0173313 A1 Aug. 11, 2005

(51) Int. Cl.
*B07C 5/02* (2006.01)

(52) U.S. Cl. .................. 209/3.1; 209/552; 209/906; 209/576

(58) Field of Classification Search ............ 209/3.1, 209/3.2, 906, 155, 552, 576, 644, 207
See application file for complete search history.

(56) References Cited

U.S. PATENT DOCUMENTS

| 3,721,255 | A | | 3/1973 | Suzuki et al. | |
|---|---|---|---|---|---|
| 4,216,477 | A | * | 8/1980 | Matsuda et al. | 417/413.3 |
| 4,756,427 | A | * | 7/1988 | Gohde et al. | 209/3.1 |
| 5,101,978 | A | * | 4/1992 | Marcus | 209/3.1 |
| 5,837,200 | A | * | 11/1998 | Diessel et al. | 422/73 |
| 6,221,654 | B1 | * | 4/2001 | Quake et al. | 435/287.3 |
| 6,497,252 | B1 | | 12/2002 | Kohler et al. | |
| 6,596,143 | B1 | * | 7/2003 | Wang et al. | 204/547 |
| 6,808,075 | B2 | * | 10/2004 | Bohm et al. | 209/172.5 |
| 6,811,133 | B2 | * | 11/2004 | Miles | 251/57 |
| 6,838,056 | B2 | * | 1/2005 | Foster | 422/100 |
| 6,929,750 | B2 | * | 8/2005 | Laurell et al. | 210/708 |
| 6,949,176 | B2 | * | 9/2005 | Vacca et al. | 204/547 |
| 2002/0036139 | A1 | * | 3/2002 | Becker et al. | 204/450 |
| 2002/0127736 | A1 | | 9/2002 | Chou et al. | |
| 2003/0027225 | A1 | * | 2/2003 | Wada et al. | 435/7.21 |
| 2004/0164650 | A1 | * | 8/2004 | Xu et al. | 310/328 |
| 2004/0214312 | A1 | * | 10/2004 | Tyvoll et al. | 435/288.4 |
| 2005/0103690 | A1 | * | 5/2005 | Kawano et al. | 209/576 |
| 2005/0272159 | A1 | * | 12/2005 | Ismagilov et al. | 436/34 |

OTHER PUBLICATIONS

"A Microfabricated Fluorescence-Activated Cell Sorter", Anne Y. Fu et al., Nature Biotechnology, vol. 17, Nov. 1999, pp. 1109-1111.
"An Integrated Microfabricated Cell Sorter", Anne Y. Fu et al., Analytical Chemistry, 2002, pp. A-G.

* cited by examiner

*Primary Examiner*—Patrick Mackey
*Assistant Examiner*—Mark Hageman

(57) ABSTRACT

A device for sorting particles. The device may include a channel structure that defines a channel having an inlet and first and second outlets. The device also may include first and second transport mechanisms. The first transport mechanism may be configured to create a particle stream of first particles and one or more second particles. Each particle may move along the channel from the inlet toward the first outlet and may be disposed in a fluid supported by the channel structure. The second transport mechanism may be configured to be pulse-activated to selectively move at least one of the second particles from the particle stream and toward the second outlet.

14 Claims, 5 Drawing Sheets

SORTING PARTICLES

BACKGROUND

Cells and other particles are often obtained as mixtures of two or more different types. For example, blood or tissue samples from patients may include a mixture of many different cell types that mask the presence or properties of a particular type of cell that is of interest. Accordingly, the cells of such samples may need to be sorted with a cell sorting device, such as a fluorescence-activated cell sorter, to identify, purify, and/or characterize cells of interest in the samples. However, cell sorters can be expensive and complex to operate and maintain.

DETAILED DESCRIPTION

A system, including method and apparatus, is provided for sorting particles, such as cells. The system may include two transport mechanisms for moving particles. A first of the transport mechanisms may be a nonselective mechanism configured to move a set of particles relatively continuously and nonselectively. The nonselective mechanism may operate, for example, by exerting a pressure on a fluid in which the set of particles is disposed and/or may exert a force on the set of particles in relation to the fluid, such as by dielectrophoresis. A second of the transport mechanisms may be a selective mechanism configured to selectively move a subset of the particles relative to other particles of the set, as the nonselective mechanism operates. Accordingly, the second transport mechanism may be pulse-activated at suitable times to selectively apply a force on particles of the subset. The force may be a pressure pulse exerted on a fluid segment in which the subset of particles is disposed. The force may be directed transversely to the direction in which the set of particles is transported by the nonselective transport mechanism, to move the subset of particles along a different path, thereby sorting the set of particles. Methods of sorting particles using a combination of selective and nonselective transport mechanisms are also disclosed.

Figure 1:
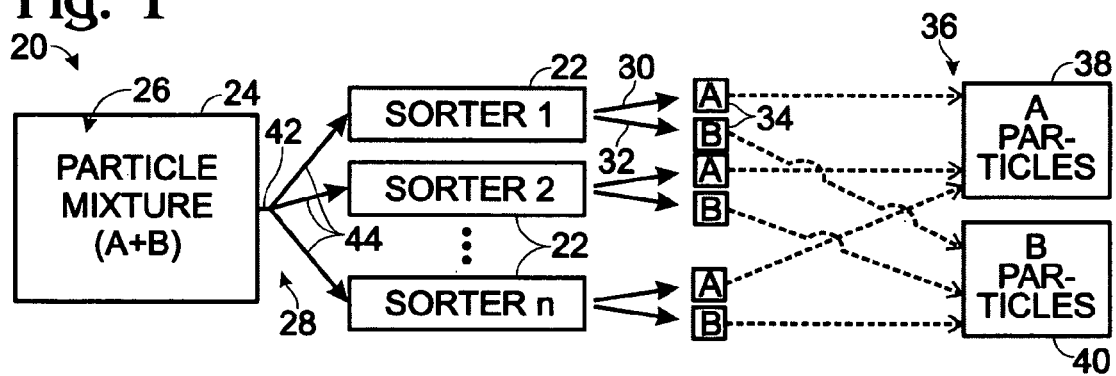
FIG. 1 is a schematic view of a system for sorting particles, in accordance with an embodiment of the invention.

FIG. 1 shows a system 20 for sorting particles using a plurality of "n" sorters 22 configured to operate in parallel. The system may include any suitable number of sorters including only one. The sorters may be disposed in parallel fluid communication with an input reservoir 24 holding an input mixture 26 of two or more types of particles, such as particles A and B, in a fluid. Fluid communication between the input reservoir and the sorters may be provided by a conduit network 28. Portions of the input mixture may be directed to the various sorters from the conduit network as separate streams of particles. Each sorter may selectively move the A and B particles of a stream along different paths 30, 32, so that the mixture is enriched for A or B particles, respectively, in different intermediate sites 34. Sorted particles of each type from each sorter may be combined, shown at 36, so that A particles and B particles are directed to their respective receiver structures 38, 40.

A sorter may be any device or mechanism for enriching a particle mixture for at least one type of particle in the particle mixture relative to other types of particles in the mixture. The sorter may be configured to move one or more types of particle from a default path of particle/fluid movement to an alternate path (or a plurality of alternate paths). Alternatively, the sorter may move different types of particles from a default path of movement to different alternate paths according to the type of particle.

The sorter may apply a force on a fluid volume or fluid segment in which a particle is disposed or may apply a force on the particle selectively in relation to the fluid volume. The force may be a pressure exerted on the fluid volume, a dielectrophoretic force on the particle, an electroosmotic force on the fluid, etc. In some embodiments, the sorter may sort by changing the path followed by fluid and particles, for example, for opening and/or closing valves, among others.

Sorters may be configured to operate concurrently, for parallel sorting from an input mixture. Alternatively, or in addition, sorters may be disposed in series for sequential sorting, for example, to provide progressive enrichment of a mixture for a particular type of particle. Enrichment, as used herein, may include any increase in the representation of one particle type relative to one or more other particle types of a mixture. For example, enrichment may increase the representation of a particular type of particle from a lower to a higher percentage of the particle total, and/or may substantially or completely separate the particular type of particle from one or more other types of particles.

An input reservoir may be any vessel (or vessels) configured to receive the input mixture and release portions of the input mixture to a sorter(s). Release of the portions may be passive, such as through passage that is always in fluid communication with the input reservoir, or active, such as with valve that operates to release portions selectively. The input reservoir may be a well, a chamber, a channel, a syringe, etc.

A conduit network may be any set of passages that provide fluid communication between the input reservoir and the sorters. The conduit network may include tubing, channels formed in or on a generally planar or three-dimensional channel structure, and/or a combination thereof, among others. The conduit network may include a set of parallel passages that extend from the input reservoir to the sorters, passages that increase in number or branch toward the sorters, or a combination thereof. For example, in the present illustration, conduit network 28 carries portions of mixture 24 in parallel through a single conduit 42 that branches to a plurality of conduits 44 equal in number to the number of sorters. The conduit network may be defined by a manifold, as described below.

An output receiver structure may be any vessel or compartment for receiving fluid and sorted particles from the sorters. Exemplary receiver structures may include microplate wells, microfluidic compartments of a chip, test tubes, culture vessels, etc. In some embodiments, each sorter may direct sorted particles to a separate receiver structure, for example, to perform post-sorting processing. The post-sorting processing may include cell culture, cell lysis, and/or molecular analysis (sensing) of cellular or particle constituents (such as analysis of a nucleic acid, protein, lipid, ion, carbohydrate, etc.). In an exemplary embodiment, post-sorting processing may include cell lysis followed by amplification of a nucleic acid.

An input mixture may include any particle mixture of interest. Particles, as used herein, may include any set of discrete, small objects. For example, the particles may be less than about 100 micrometers in diameter, and may be biological, synthetic, naturally occurring, organic, inorganic, or a combination thereof. Exemplary particles may include cells. The cells may be alive or dead, fixed or unfixed, processed or unprocessed, cultured or noncultured, and/or the like. Exemplary cells may include eukaryotic cells and/or bacteria. Other exemplary particles may include viruses, organelles, vesicles, synthetic polymers, beads, coded beads carrying biomolecules, magnetic particles, and/or the like.

Exemplary sources for particle mixtures may include a patient sample (such as blood, a tissue biopsy, mucus, saliva, urine, sperm, tears, sweat, etc.), an environmental sample (such as a sample from water, air, soil, etc.), and/or a research sample, among others.

The input mixture may be preprocessed before sorting. For example, the input mixture may be treated to make a subset of the particles optically distinguishable. In some embodiments, the mixture may be treated with a dye to selectively label a subset of the particles. The dye may be any optically detectable material. The dye may bind directly to the particles or bind through a coupled (covalently or noncovalently) specific binding member, such as an antibody, a lectin, a molecular imprinted polymer, a nucleic acid, a receptor, a ligand, etc. Alternatively, or in addition, the input mixture may be cells that have been engineered, such as by transfection, to express an optically detectable material, such as green fluorescent protein.

Figure 2:
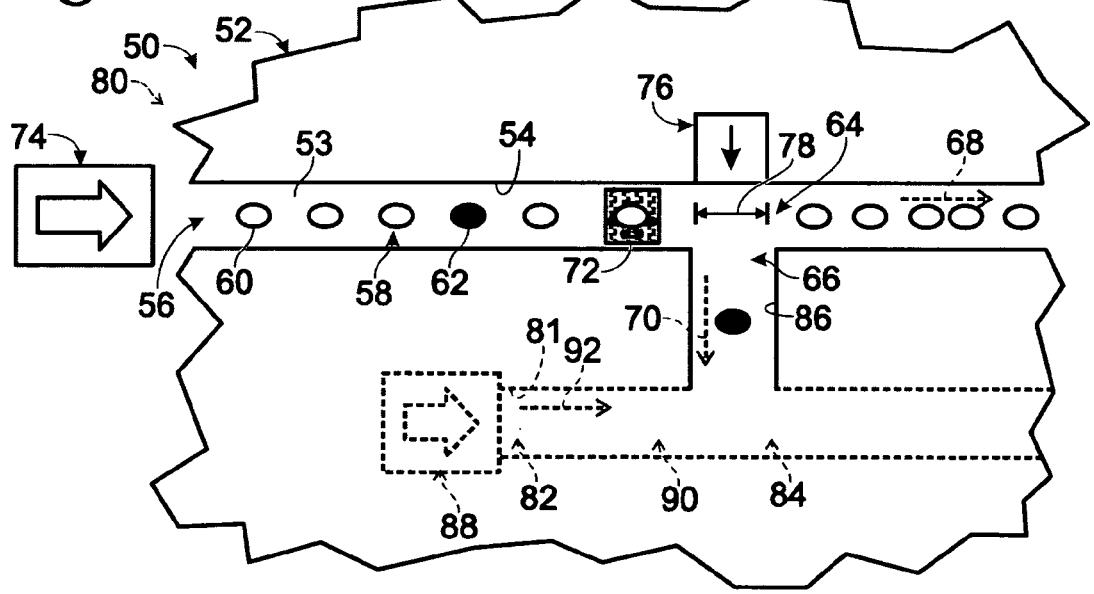
FIG. 2 is a schematic view of a sorter unit that may be included in the system of FIG. 1, in accordance with an embodiment of the invention.

FIG. 2 shows an example of a sorter unit 50 that may be included in system 20. Sorter unit 50 may include a channel structure 52 defining at least one channel 54. Channel structure 52 may be any structure that defines a passage along which particles (and fluid 53) may be transported. The passage may be any predefined path for particle/fluid travel. In addition, the passage may include walls and/or a particle guiding and/or fluid guiding surface characteristic, such as adjacent hydrophobic and hydrophilic surface regions. The channel structure may support the particles by supporting fluid in which the particles are disposed. Supported fluid, as used herein, is fluid that is in contact with a solid surface so that the fluid is restricted from falling. By contrast, unsupported fluid may include airborne fluid droplets. In some embodiments, the channel structure may be a substrate assembly including a substrate and a fluid barrier connected to the substrate, as described further below.

Channel 54 may include an inlet 56 at which a stream 58 of particles 60, 62 may be received, and first and second outlets 64, 66 to which the particles may travel. Accordingly, channel 54 may be described as a branched channel because particles and/or fluid may travel along two or more different paths 68, 70 through the channel.

Sorter unit 50 also may include a sensor 72 configured to sense a property of each particle 60, 62. The sensor may be an optical sensor that measures an optical (or electromagnetic) property of each particle, such as a luminescence (photoluminescence (for example, fluorescence or phosphorescence), chemiluminescence, or bioluminescence), scattering, absorbance, refraction, reflection, and/or polarization, among others. Alternatively, the sensor may be an electrical or magnetic sensor, configured to sense an electrical or magnetic property of the particles, respectively.

Sensor 72 may have any suitable size, shape, location, and structure. In some embodiments, the sensor may be longer than the diameter of the particles, that is, long enough to sense a particle at a plurality positions along the channel, for example, to measure the velocity of the particle. Accordingly, the sensor may be a single sensor or a plurality of sensor elements, which may be arrayed, for example, along the channel. The sensor also may have any suitable width including a width substantially similar to the width of the channel. The sensor may be formed on or below a surface of the channel, for example, one or more photodiodes formed on or in a substrate that defines a floor of the channel. The photodiodes may be configured to receive light selectively. Accordingly, they may be coated with a photoselective material, such as a filter layer that selectively permits the passage of particular wavelengths of light.

Sorter unit 50 may include, and/or function with, a plurality of mechanisms for moving particles and/or fluid, such as nonselective and selective transport mechanisms 74 and 76, respectively.

Nonselective transport mechanism 74 may be any mechanism(s) for moving input particles relatively nonselectively through channel 54. The nonselective transport mechanism may exert a similar force on different types of particles in a particle mixture so that they travel with a similar velocity. Alternatively, the nonselective transport mechanism may exert dissimilar forces so that different particles travel with different velocities. However, in either case, the nonselective transport mechanism moves the particles through the channel. The nonselective transport mechanism may be a continuous transport mechanism. A continuous transport mechanism, as used herein, may be any transport mechanism that moves a plurality of particles through the channel without substantial interruption.

In the present illustration, nonselective transport mechanism 74 sends a stream 58 of particles 60, 62 into and through the channel to default path 68 (without operation of selective transport mechanism 76). A stream, as used herein, is a succession of moving particles created by entry into, and movement of the particles along, the channel. The succession may be relatively steady or intermittent and may introduce particles into the channel one by one, that is, in single file, or two or more at once in a side-by-side or random arrangement, among others. In some embodiments, the diameter of the channel may be small enough to restrict the particles to movement in single file.

The nonselective transport mechanism may operate by any suitable mechanism. For example, the nonselective transport mechanism may operate by exerting a force on a fluid in which the particles are disposed, to promote bulk fluid flow and concomitant bulk particle flow. Alternatively, this transport mechanism may exert a force on the particles relative to the fluid, to promote bulk particle flow through the fluid. The nonselective transport mechanisms may apply a positive or negative pressure to the fluid, generally upstream (toward the input mixture) or downstream (toward the receiver structures), respectively, of channel 54, so that there is a pressure drop along the channel. Exemplary nonselective transport mechanisms may include pressurized gas, a positive displacement pump (such as a syringe pump), a vacuum, and/or a peristaltic pump, among others. Other exemplary nonselective transport mechanisms may include electrodes arrayed to provide dielectrophoretic-based movement of the particles, for example, using traveling wave dielectrophoresis to propel a mixture of particles along the channel.

Sorter 50 also may include selective transport mechanism 76 that cooperates with nonselective transport mechanism 74. The selective transport mechanism may be any mechanism(s) configured to selectively move a subset of one or more particles of a mixture along a different path than other particles of the mixture.

The selective transport mechanism may be configured to act on individual particles or sets of particles of the mixture. In some embodiments, the particles of stream 58 may be spaced sufficiently so that single particles may be displaced from the stream. Alternatively, the particles may not be spaced sufficiently, so that two or more particles may be displaced together. In either case, an enrichment of the mixture for a particular type(s) of particle, particularly a minor particle, may occur.

The selective transport mechanism may be pulse-activated, to provide a transient action on selected particles. Pulse-activated, as used herein, means activated by a transient signal pulse or a by a plurality of transient signal pulses. The transient signal pulses may be produced as needed to sort particles, generally separated by irregular time intervals, rather than being a steady signal or periodic signals occurring at regular intervals. Exemplary signal(s) may be an electrical signal (such as a current or voltage pulse) or an optical pulse that activates a phototransistor, among others.

The transient action on the selected particles and/or the transient signal pulses that activate the transport mechanism may be fast, that is, lasting for less than about one second. In some examples, the transient action may be a pressure pulse that lasts less than about ten milliseconds or less than about one millisecond, depending on parameters such as fluid viscosity, channel dimensions, channel geometry, etc.

The selective transport mechanism may have any suitable maximum frequency of transport. The maximum frequency of transport is the maximum frequency of pressure pulses that can be produced per second and therefore the maximum number of particles that can be displaced by the selective transport mechanism per second. In some examples, the maximum frequency may be at least about 100 hertz or at least about one kilohertz.

Selective mechanism 76 may be configured to operate concurrently with nonselective mechanism 74, that is, selective transport mechanism 76 may displace selected particles 62 from a particle stream created by operation of the nonselective transport mechanism. In some embodiments, the selective transport mechanism may be configured to exert a pressure pulse locally on a fluid volume in channel 54, for example, on a fluid segment or fraction 78 disposed adjacent second outlet 66, to direct particles 62 along second path 70.

Exemplary selective transport mechanisms may be formed by thin-film electrical devices, such as thin-film heaters (for example, resistive layers) and piezoelectric elements, among others. Such thin-film electrical devices may be actuated rapidly with an actuation pulse to provide a transient pressure pulse. Thin-films, as used herein, are any films that are formed on a substrate. The thin-films may be formed by any suitable method, such as vapor deposition, sputtering, magnetron-based deposition, and/or plasma-enhanced deposition, among others. Individual layers of the thin-films may have any suitable thickness, or a thickness of less than about 500 µm, 100 µm, or 20 µm. Alternatively, or in addition, the individual thin-film layers may have a thickness of greater than about 10 nm, 20 nm, or 50 nm.

Alternative sorter unit 80, also including portions shown here in phantom outline, may include a second channel 81 disposed adjacent first channel 54. Second channel 81 may include an inlet 82 and an outlet 84. First and second channels 54, 81 may be in fluid communication, for example, connected by a passage 86. Second channel 81 may be operated upon by a fluid transport mechanism 88 configured to send a stream of another fluid 90 along a third path 92, which may be substantially parallel to first path 68. Accordingly, particles displaced from stream 58 into passage 86 may join fluid stream 90 and exit channel 81 through outlet 84.

The same reference indicators are used to refer to the same system components throughout the discussion of FIGS. 3-10 below. Thus, to make it easier to understand the relationship between different drawings, selected drawings may include reference indicators for system components that are discussed primarily or exclusively in the context of other drawings.

Figure 3:
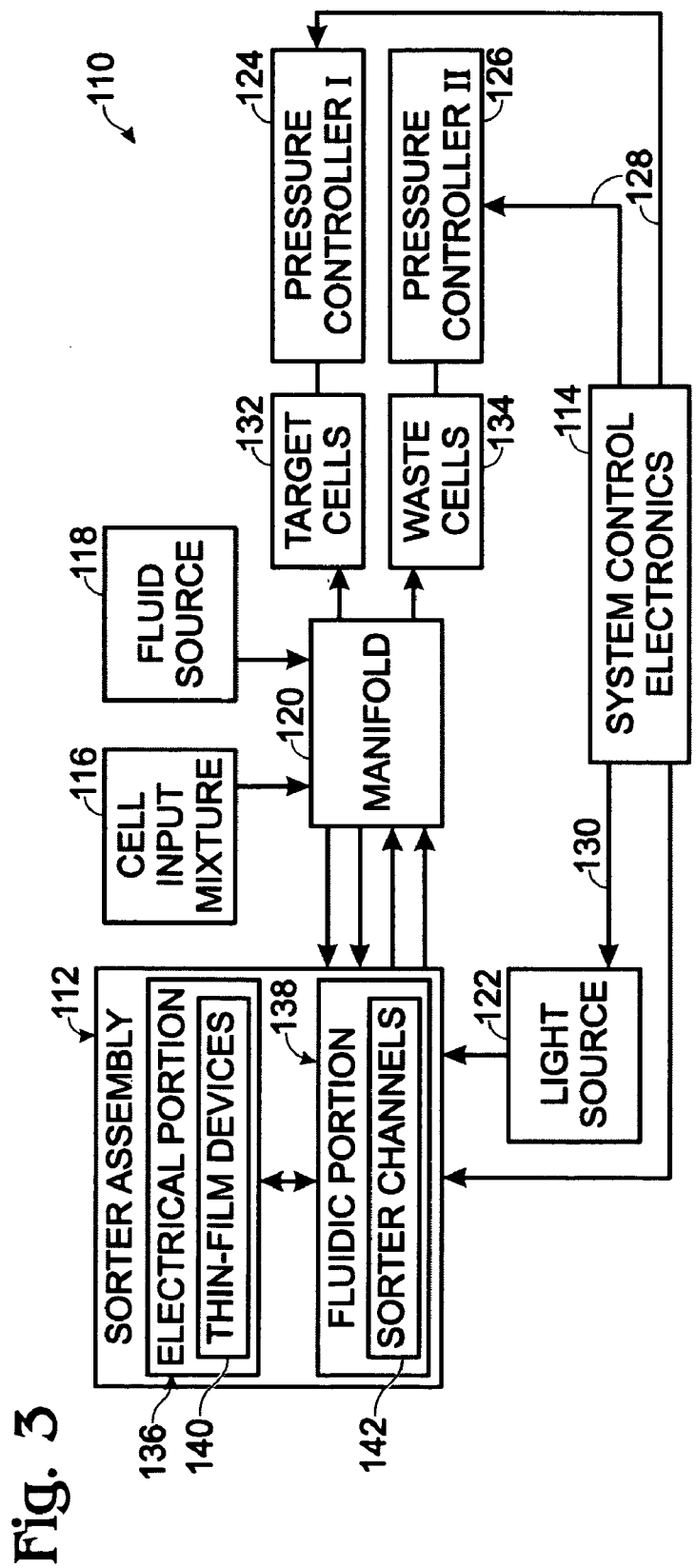
FIG. 3 is a schematic view of another system for sorting particles and particularly cells, in accordance with an embodiment of the invention.

FIG. 3 shows a schematic view of a system 110 for sorting cells or other particles. System 110, and other sorter systems described by the present teachings, may provide environmental isolation of biological material, such as isolation of potentially hazardous material from a user of the system.

System 110 may include a sorter assembly 112. The sorter assembly may be interfaced electrically with system control electronics 114 and a processor included therein. The sorter assembly also may be interfaced fluidically with a cell input mixture 116 and, optionally, a separate fluid source 118, through a manifold 120 for routing fluid. Furthermore, the sorter assembly may be interfaced optically with a light source 122. Cells and fluid may be moved from cell input mixture 116 and fluid source 118 by one or more particle/fluid transport mechanisms, such as pressure controllers 124, 126, which may apply a negative pressure downstream from sorter assembly 112 and manifold 120. The pressure controllers and the light source also may be interfaced with the system control electronics, shown at 128, 130, to provide, for example, processor-based control of fluid/particle transport and light exposure. Accordingly, light source 122 may be a constant source or a pulsed source, among others.

In operation, cells of input mixture 116 may enter and exit sorter assembly 112 via manifold 120, before and after sorting, respectively. When the cells exit the sorter assembly and manifold, they may represent enriched populations, such as target cells 132 and waste cells 134. In various embodiments, the target cells may be re-sorted, cultured, and/or analyzed molecularly or on a cellular level, among others. Waste cells 134 may be discarded. Alternatively, the "waste" cells may be another population of interest to be processed further.

Sorter assembly 112, also termed a substrate assembly, may include an electrical portion 136 interfaced with a fluidic portion 138. Electrical portion 136 may include a plurality of thin-film devices 140, such as switching devices (transistors, diodes, etc.), temperature control devices (heaters, coolers, temperature sensors, etc.), transducers, sensors, etc. Accordingly, electrical portion 136 may be an electronic portion with flexible circuitry. Fluidic portion 138 may define a plurality of sorter channels 142 that create the fluidic aspects of the sorter units.

Figure 4:
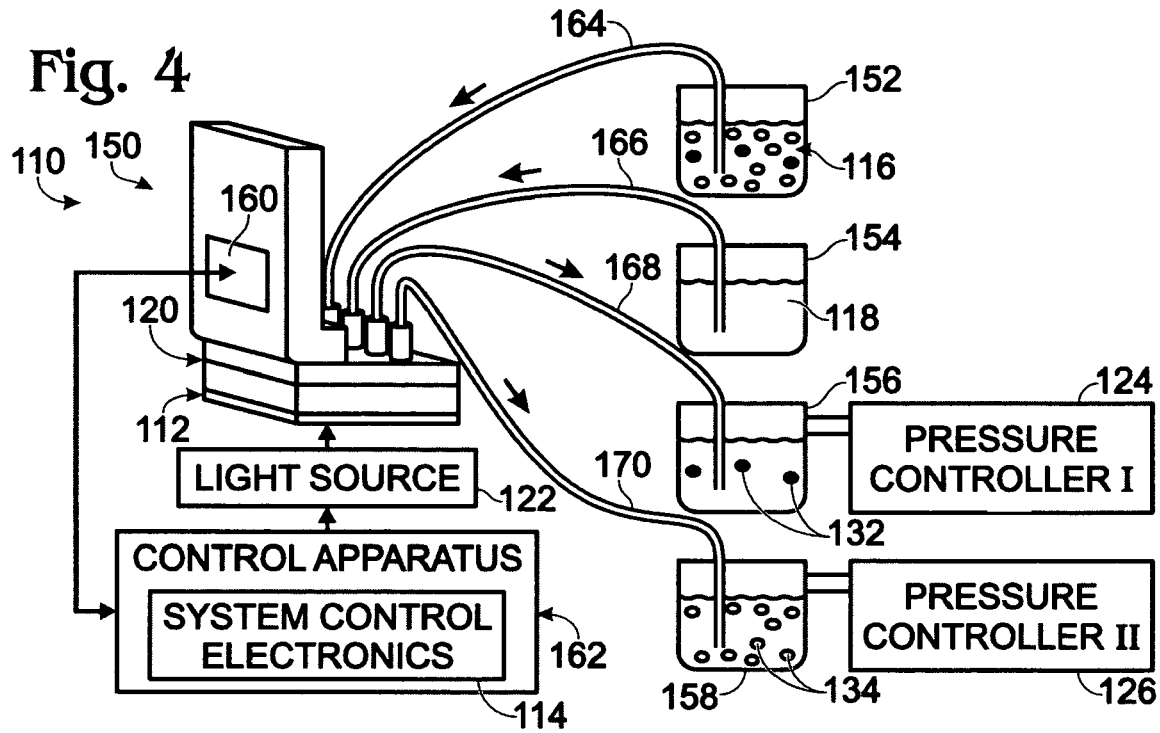
FIG. 4 is a partially schematic view of the system of FIG. 3, in accordance with an embodiment of the invention.

FIG. 4 is a partially schematic view of system 110. System 110 may include a sorter device 150 that includes sorter assembly 112 connected adjacent manifold 120. Sorter device 150 also may include one or more input reservoirs 152, 154, output reservoirs 156, 158, and pressure controllers 124, 126. The input and output reservoirs may be any suitable vessels or fluid receiver structures. The sorter device also may include system control electronics 114 and light source 122. Alternatively, the system control electronics, light source, pressure controllers, and/or one or more reservoirs may be separate from the sorter device. For example, sorter device 150 may be configured as a reusable or single-use cartridge that electrically couples through an electrical interface 160 to a control apparatus 162.

Sorter device 150 may function in system 110 as follows. Cell input mixture 116 and fluid 118 may be pulled into sorter assembly 112 due to negative pressure exerted by pressure controllers 124, 126. The cell mixture and fluid may travel from cell and fluid input reservoirs 152, 154, through respective conduits 164, 166 and manifold 120 into sorter assembly 112. Without any sorting by the sorter assembly, portions of fluid 118 from fluid input reservoir 154 may pass back through the manifold to be received in target reservoir 156 from conduit 168. In addition, portions of input mixture 116 may be received in waste reservoir 158 from conduit 170. However, the action of sorter assembly 112 displaces target cells 132 from mixture 116 so that they are placed selectively in target reservoir 156.

Figure 5:
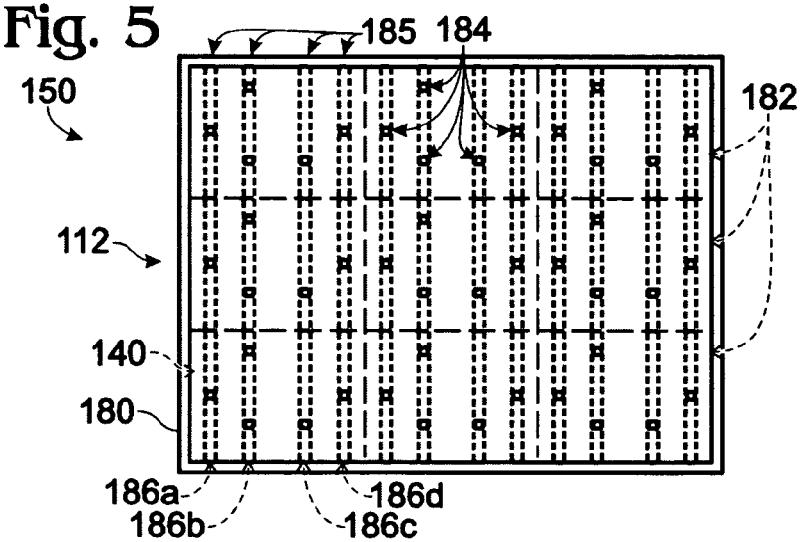
FIG. 5 is a bottom view of selected portions of a substrate assembly included in the system of FIG. 4, in accordance with an embodiment of the invention.

FIG. 5 shows a bottom view of selected portions of sorter assembly 112 of sorting device 150. The sorter assembly may include a substrate 180 having a plurality of thin-film electrical devices 140. The sorter assembly also may include a plurality of sorter units 182, delineated here generally as a three-by-three array of dashed boxes. The substrate may define a plurality of openings, such as feed holes 184, through which fluid and particles may pass, to and/or from the adjacent manifold 120 (see FIG. 4). Feed holes 184 may be arranged in columns, shown at 185. Each column 185 may be aligned with a first-layer manifold conduit, such as conduits 186a-186d, which are shown in dashed outline and disposed adjacent an opposing surface of the substrate. Manifold conduits are described in more detail in relation to FIGS. 7-9. A fluid barrier that cooperates with the substrate to form channels is disposed adjacent the substrate but is shown elsewhere (see FIGS. 6 and 7).

Substrate 180 may have any suitable structure and composition. In some embodiments, the substrate may be generally planar. The substrate may be formed of a semiconductor, such as silicon or gallium arsenide, among others, or of an insulator, such as glass or ceramic. Accordingly, thin-film devices may be fabricated in and/or on a semiconductor, or on an insulator, for example, by flat panel technology. The substrate may provide feed holes 184, so that the manifold is disposed adjacent a substrate surface that opposes the thin-film devices. Alternatively, feed holes 184 may be defined above the substrate. adjacent the same substrate surface as the thin-film devices. Accordingly, a fluid barrier disposed connected to the substrate adjacent the thin-film devices may interface with the manifold (see below).

The sorter assembly may include any suitable number of sorter units in any suitable arrangement. For example, the sorter assembly may include more than ten or more than one-hundred sorter units. In some embodiments, the sorter units may be arranged in a two-dimensional array, which may be rectilinear, among others.

Figure 6:
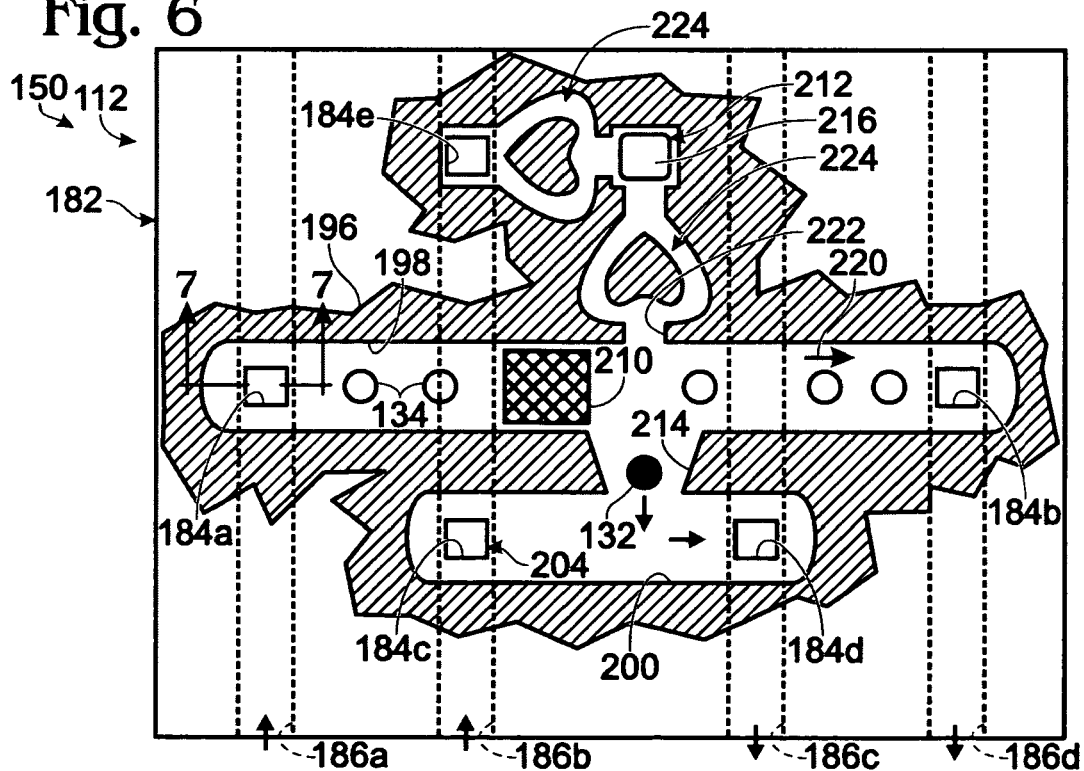
FIG. 6 is a fragmentary bottom view of a sorter unit included in the substrate assembly of FIG. 5, as the sorter unit sorts cells, in accordance with an embodiment of the invention.

FIG. 6 shows a sorter unit 182 included in sorter assembly 112, as the sorter unit sorts cells 132, 134. A fluid barrier 196, shown here in fragmentary sectional view, may be connected to substrate 180 to define the walls of adjacent channels 198, 200 that receive fluid and/or cells. In particular, channel 198 may receive fluid carrying cells 132, 134 from first manifold conduit 186a and through feed hole 184a. The cells may travel along the channel to exit at feed hole 184b, which communicates with fourth manifold conduit 186d. Channel 200 may receive a fluid from second manifold conduit 186b and feed hole 184c, shown at 204. The fluid may travel along channel 200 to exit at hole 184d, which communicates with third manifold conduit 186c.

Sorter unit 182 may include a sensor 210 and a transport mechanism 212 that is selectively actuated based on information from the sensor. Sensor 210 may be disposed upstream of a passage 214 that connects channels 198, 200. The sensor may sense a property of each cell that passes over the sensor. If the property meets a predefined criterion, transport mechanism 212 may be actuated at a suitable time after sensing the cell, for example, based on a predicted arrival time of the cell adjacent passage 214.

Transport mechanism 212 may include a thin-film electrical device 216 that displaces selected cells from channel 198 when pulse-activated. Electrical device 216 may be a thin-film heater or a piezoelectric element, among others. Thin-film device may exert a force transverse to channel 198, that is, transverse to a default path 220 along which the cells travel. The force may be directed selectively toward passage 214, from an opposing passage 222, by the use of fluid diodes 224. The fluid diodes may be any conduit structure that selectively restricts flow in one direction, for example, upward from channel 198 in the present illustration. Other exemplary fluid diodes that may be suitable are included in U.S. Pat. No. 4,216,477 to Matsuda et al., which is incorporated herein by reference.

Fluid moved by a pressure pulse from transport mechanism 212 may be supplied by feed hole 184e, which communicates with second manifold conduit 186b, or from a separate fluid source. The pressure pulse may displace cell 132 from upper channel 198 to lower channel 200. The cell then may join fluid flowing in channel 200 to exit at feed hole 184d.

Figure 7:
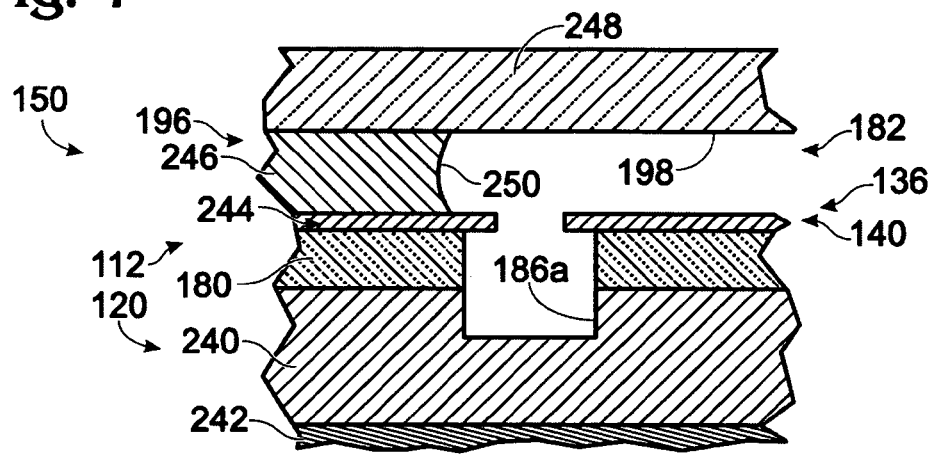
FIG. 7 is a fragmentary sectional view of the sorter unit of FIG. 6, taken generally along line 7-7 of FIG. 6, in accordance with an embodiment of the invention.

FIG. 7 shows a sectional view of the sorter unit 182 and adjacent regions of sorter device 150. Substrate assembly 112 may adjoin manifold 120, particularly a first manifold layer 240 that defines first manifold conduit 186a. A second manifold layer 242 may be spaced from the substrate assembly.

Substrate assembly 112 may include substrate 180, thin-film layers 244 formed adjacent the substrate's surface (in or on the substrate), and fluid barrier 196 connected to the substrate and thin-film layers. The thin-film layers may define electrical portion 136 of the substrate assembly. particularly thin-film electrical devices 140 thereof. Fluid barrier 196 may be formed unitarily or, as shown in the present illustration, may be formed of a channel layer 246, and a cover layer 248. The channel layer may define walls 250 of channel 198. Channel layer 246 may be formed from any suitable material, including, but not limited to, a negative or positive photoresist (such as SU-8 or PLP), a polyimide, a dry film (such as DUPONT Riston®), and/or a glass. Methods for patterning the channel layer 246 may include photolithography, micromachining, molding, stamping, laser etching, and/or the like. Cover layer 248 also may define a wall of channel 198. The cover layer may be formed of an optically transparent material, such as glass or plastic, to permit light from the light source to enter channel 198.

Figure 8:
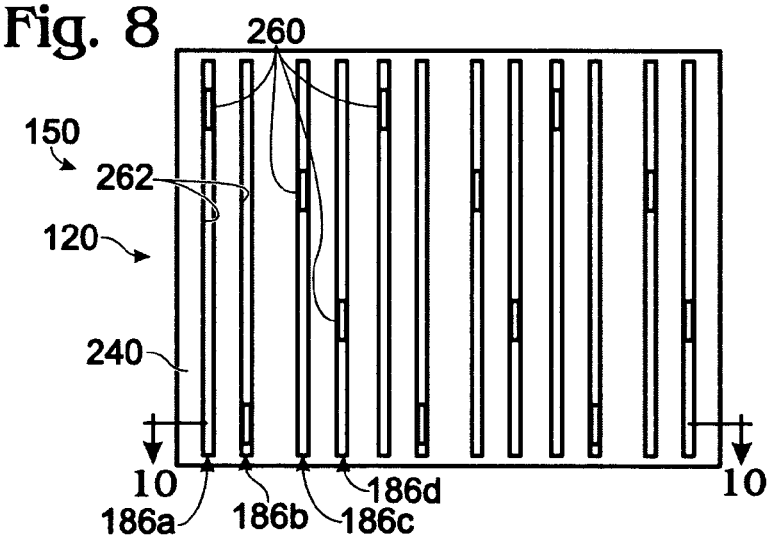
FIG. 8 is a bottom view of a manifold disposed above the substrate assembly of FIG. 5 in the system of FIG. 4, in accordance with an embodiment of the invention.

FIG. 8 shows a bottom view of first manifold layer 240 of manifold 120. Manifold layer 240 may include a plurality of openings 260 extending through the manifold layer and aligned with manifold conduits, such as first-layer manifold conduits 186a-d defined by grooves 262 of the first manifold layer in abutment with substrate 180 (see FIG. 5). Accordingly, openings 260 are disposed in fluid communication with columns 185 of feed holes 184 (see FIG. 5) via the first-layer manifold conduits.

Figure 9:
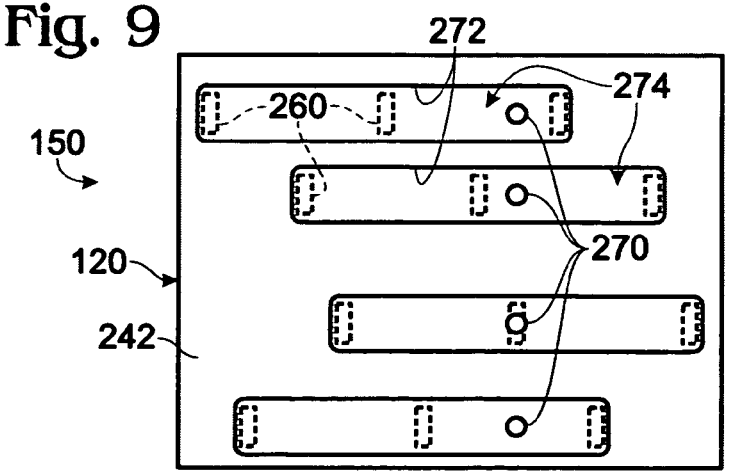
FIG. 9 is a bottom view of an upper layer of the manifold of FIG. 8, in accordance with an embodiment of the invention.

FIG. 9 shows a bottom view of a second layer 242 of manifold 120. Second layer 242 may include second-layer openings 270 extending through the second layer from grooves 272 formed in the second layer. Each groove 272 may be configured to be aligned with a row of first-layer openings 260 from first manifold layer 240 (see FIG. 8). First-layer openings 260 are shown in phantom outline in this view to simplify the presentation. Each groove 272 may form a second-layer conduit 274 by abutment of the first and second manifold layers. Each second-layer conduit 274 may provide fluid communication between a row of first-layer openings 260 and thus a plurality of corresponding columns of feed holes 184 in the substrate (see FIG. 5).

Figure 10:
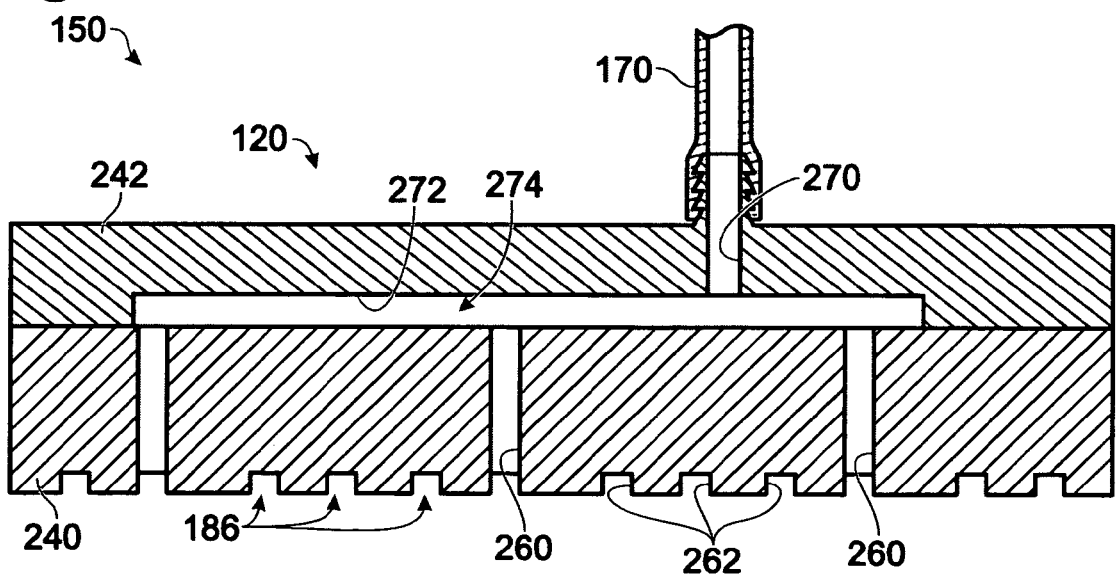
FIG. 10 is a sectional view of the manifold of FIG. 8, in accordance with an embodiment of the invention.

FIG. 10 shows a sectional view of manifold 120 of sorter device 150. Fluid may travel from columns of substrate feed holes (see FIG. 5), through first-layer conduits 186, and then through a second layer conduit 274 to tubing 170.

The devices and methods described herein may be microfluidic devices and methods. Microfluidic devices and methods receive, manipulate, and/or analyze samples in very small volumes of fluid (liquid and/or gas). The small volumes are carried by one or more passages, at least one of which may have a cross-sectional dimension or depth of between about 0.1 to 500 µm, or less than about 100 µm or 50 µm. Accordingly, fluid at one or more regions within microfluidic devices may exhibit laminar flow with minimal turbulence, generally characterized by a low Reynolds number. Microfluidic devices may have any suitable total fluid capacity.

It is believed that the disclosure set forth above encompasses multiple distinct embodiments of the invention. While each of these embodiments has been disclosed in specific form, the specific embodiments thereof as disclosed and illustrated herein are not to be considered in a limiting sense as numerous variations are possible. The subject matter of this disclosure thus includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

What is claimed is:

1. A device for sorting particles, comprising:
a substrate assembly including a substrate, a plurality of thin-film electrical devices formed on the substrate, and a fluid barrier connected to the substrate such that the substrate assembly defines a channel having an inlet and first and second outlets, the channel and the thin-film electrical devices being disposed generally between the substrate and the fluid barrier;
a first transport mechanism configured to move first particles and one or more second particles in the channel from the inlet toward the first outlet, the first particles and one or more second particles being disposed in a fluid; and
a second transport mechanism configured to apply a transient pressure pulse on the fluid so that at least one of the second particles is selectively moved toward the second outlet,
wherein the second transport mechanism includes a thin-film heater element, a thin-film piezoelectric element, or both, and wherein the thin-film heater, the thin-film piezoelectric element, or both are included in the thin-film electrical devices.

2. The device of claim 1, wherein the first transport mechanism is configured to create a flow of the fluid through the channel, and wherein the flow of the fluid carries the first particles and one or more second particles.

3. The device of claim 2, wherein the second transport mechanism is configured to apply the transient pressure pulse to a segment of the fluid in which the at least one second particle is disposed.

4. The device of claim 1, wherein the channel structure is configured so that the first particles and one or more second particles follow a path from the inlet to the first outlet without operation of the second transport mechanism, and wherein the transient pressure pulse is directed transverse to the path.

5. The device of claim 1, wherein the substrate assembly defines
first and second channels that extend adjacent one another and between respective pairs of opposing ends of the first and second channels, the substrate assembly further defining a transverse channel that connects the first channel to the second channel intermediate the pair of opposing ends of each channel,
wherein the first transport mechanism is configured to send respective first and second streams through the first and second channels, the first stream including first particles and one or more second particles, and
wherein the second transport mechanism is configured to selectively move at least one of the second particles from the first stream in the first channel to the second stream in the second channel via the transverse channel.

6. The device of claim 1, wherein the first particles and the one or more second particles are different types of cells.

7. The device of claim 5, wherein the first stream follows a path, and wherein the second transport mechanism is configured to apply transient pressure pulses to the first stream and transverse to the path.

8. The device of claim 1, wherein the second transport mechanism includes a thin-film heater.

9. The device of claim 5, wherein the transverse channel provides the same path between the first and second channels whether or not the second transport mechanism is selectively moving a second particle.

10. The device of claim 1,
wherein the substrate assembly defines a passage disposed in fluid communication with the channel and generally opposing the second outlet, and wherein the passage includes a fluid diode configured to restrict fluid backflow created by operation of the second transport mechanism.

11. The device of claim 1, wherein the first transport mechanism is configured to produce a pressure drop along the channel.

12. The device of claim 1, wherein the substrate assembly is configured so that the particles follow a path from the inlet to the first outlet without operation of the second transport mechanism, and wherein the second transport mechanism is configured to exert pressure pulses directed transverse to the path.

13. The device of claim 1, wherein the channel is a first channel and the inlet is a first inlet, the substrate assembly defining a second channel adjacent to the first channel and configured to carry fluid from a second inlet to a third outlet, and wherein the second outlet of the first channel places the first channel in fluid communication with the second channel.

14. The device of claim 1, further comprising an optical sensor configured to sense the at least one second particle and coupled to the second transport mechanism so that sensing the at least one second particle actuates the second transport mechanism.

* * * * *